US011819624B2

(12) United States Patent
Allen et al.

(10) Patent No.: US 11,819,624 B2
(45) Date of Patent: Nov. 21, 2023

(54) SYSTEMS AND METHODS OF TRANSFORMING FLUID FLOW OF AN INHALANT ANESTHETIC TO EXPEDITE PATIENT RECOVERY

(71) Applicants: Jeff Allen, Parkland, FL (US); Paul Robert Gardiner, West Sussex (GB)

(72) Inventors: Jeff Allen, Parkland, FL (US); Paul Robert Gardiner, West Sussex (GB)

(73) Assignee: Noble Aesthetics, LLC, Parkland, FL (US)

(*) Notice: Subject to any disclaimer, the term of this patent is extended or adjusted under 35 U.S.C. 154(b) by 690 days.

(21) Appl. No.: 16/898,221

(22) Filed: Jun. 10, 2020

(65) Prior Publication Data

US 2021/0046275 A1 Feb. 18, 2021

Related U.S. Application Data

(60) Provisional application No. 62/887,706, filed on Aug. 16, 2019.

(51) Int. Cl.
*A61M 19/00* (2006.01)
*A61M 16/00* (2006.01)
*A61M 16/06* (2006.01)

(52) U.S. Cl.
CPC .......... *A61M 19/00* (2013.01); *A61M 16/022* (2017.08); *A61M 16/06* (2013.01); *A61M 2016/0027* (2013.01); *A61M 2016/0039* (2013.01); *A61M 2202/0208* (2013.01); *A61M 2202/0283* (2013.01); *A61M 2205/3334* (2013.01)

(58) Field of Classification Search
CPC .... A61M 19/00; A61M 16/06; A61M 16/022; A61M 16/104; A61M 2202/0283; A61M 2202/0241; Y02C 20/10
See application file for complete search history.

(56) References Cited

U.S. PATENT DOCUMENTS

| 7,836,882 | B1 * | 11/2010 | Rumph | ............. | A61M 16/0093 |
| | | | | | 128/204.21 |
| 2015/0075525 | A1 * | 3/2015 | Ahearn | ............... | A61M 16/024 |
| | | | | | 128/203.14 |
| 2016/0228670 | A1 * | 8/2016 | Av-Gay | ............... | A61M 16/12 |
| 2016/0310918 | A1 * | 10/2016 | Baldus | ............... | G06F 11/0745 |

* cited by examiner

*Primary Examiner* — Philip R Wiest
*Assistant Examiner* — Nathan M Le
(74) *Attorney, Agent, or Firm* — Kaufman & Canoles, P.C.

(57) ABSTRACT

Systems and methods of controlling fluid flow of an inhalant anesthetic to expedite patient recovery are provided such that nitrous oxide flow and oxygen flow over different durations are output to a patient mask. In one exemplary embodiment, a method performed by a controller in an inhalant anesthetic system that outputs a nitrous oxide flow and an oxygen flow over different durations for output to a patient mask comprises sending, to a nitrous oxide flow control mechanism, an indication to enable the nitrous oxide flow for a first predetermined duration that corresponds to a certain amount of nitrous oxide. Further, the method includes sending, by the controller, to the oxygen flow control mechanism, an indication to enable the oxygen flow for a second predetermined duration that corresponds to a certain amount of oxygen.

20 Claims, 6 Drawing Sheets

200

```
┌─────────────────────────────────────────────────────────────────────┐
│ BY A CONTROLLER IN AN INHALANT ANESTHETIC SYSTEM THAT COMBINES A    │
│ NITROUS OXIDE FLOW AND AN OXYGEN FLOW FOR OUTPUT TO A PATIENT MASK, │─ 201
│ RECEIVE, FROM A PATIENT RECOVERY INITIATION CIRCUIT THAT IS         │
│ OPERATIONALLY COUPLED TO THE CONTROLLER, AN INDICATION TO PROVIDE   │
│ ONLY THE OXYGEN FLOW TO THE MASK SO AS TO EXPEDITE PATIENT RECOVERY │
│ FROM INHALATION OF THE NITROUS OXIDE                                │
└─────────────────────────────────────────────────────────────────────┘
                                    ▼
┌─────────────────────────────────────────────────────────────────────┐
│ DETERMINE TO PROVIDE ONLY THE OXYGEN FLOW TO THE MASK BASED ON THE  │─ 203
│                          RECEIVED INDICATION                        │
└─────────────────────────────────────────────────────────────────────┘
                                    ▼
┌─────────────────────────────────────────────────────────────────────┐
│ ACTIVATE A TIMER FOR A PREDETERMINED DURATION THAT CORRESPONDS TO   │─ 205
│      PROVIDING A CERTAIN AMOUNT OF OXYGEN THROUGH THE MASK          │
└─────────────────────────────────────────────────────────────────────┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ SEND, TO A NITROUS OXIDE FLOW CONTROL MECHANISM THAT IS             │
│ OPERATIONALLY COUPLED TO THE CONTROLLER, AN INDICATION TO ENABLE    │─ 207
│ THE FLOW OF NITROUS OXIDE TO THE MASK, WHEREIN THE NITROUS OXIDE    │
│ FLOW CONTROL MECHANISM IS OPERABLE TO CONTROL THE NITROUS OXIDE     │
│ FLOW TO THE MASK                                                    │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ RECEIVE, FROM A NITROUS OXIDE FLOW METER THAT IS OPERATIONALLY      │
│ COUPLED TO THE CONTROLLER, AN INDICATION OF A PRESSURE MEASUREMENT  │─ 209
│ ASSOCIATED WITH THE NITROUS OXIDE FLOW, WHEREIN THE NITROUS OXIDE   │
│ FLOW METER IS DISPOSED BETWEEN THE NITROUS OXIDE FLOW CONTROL       │
│ MECHANISM AND THE MASK                                              │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ DETERMINE THAT THE NITROUS OXIDE FLOW CONTROL MECHANISM IS          │─ 211
│ CONFIGURED TO DISABLE THE NITROUS OXIDE FLOW TO THE MASK BASED ON   │
│ THE MEASUREMENT                                                     │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ SEND, TO AN INDICATOR DEVICE OPERATIONALLY COUPLED TO THE           │─ 213
│ CONTROLLER, AN INDICATION THAT ONLY THE OXYGEN FLOW IS OUTPUT TO    │
│ THE MASK                                                            │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ IN RESPONSE TO DETERMINING THAT THE TIMER HAS EXPIRED, SEND, TO AN  │─ 215
│ OXYGEN FLOW CONTROL MECHANISM THAT IS OPERATIONALLY COUPLED TO THE  │
│ CONTROLLER, AN INDICATION TO DISABLE THE FLOW OF OXYGEN             │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

┌─────────────────────────────────────────────────────────────────────┐
│ BY A CONTROLLER IN AN INHALANT ANESTHETIC SYSTEM THAT OUTPUTS A NITROUS │
│ OXIDE FLOW AND AN OXYGEN FLOW OVER DIFFERENT DURATIONS FOR OUTPUT TO A │ ⎯ 501
│ PATIENT MASK, SEND, TO A NITROUS OXIDE FLOW CONTROL MECHANISM, AN │
│ INDICATION TO ENABLE THE NITROUS OXIDE FLOW FOR A FIRST PREDETERMINED │
│ DURATION THAT CORRESPONDS TO PROVIDING A CERTAIN AMOUNT OF NITROUS │
│ OXIDE THROUGH THE MASK │
└─────────────────────────────────────────────────────────────────────┘
                                    ↓
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│               ACTIVATE A TIMER FOR THE FIRST DURATION               │ ⎯ 503
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ↓
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ IN RESPONSE TO DETERMINING THAT THE TIMER FOR THE FIRST DURATION HAS │ ⎯ 505
│ EXPIRED, SEND, TO THE NITROUS OXIDE FLOW CONTROL MECHANISM, AN INDICATION │
│                    TO DISABLE THE NITROUS OXIDE FLOW                │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ↓
┌─────────────────────────────────────────────────────────────────────┐
│ SEND, TO THE OXYGEN FLOW CONTROL MECHANISM, AN INDICATION TO ENABLE THE │ ⎯ 507
│ OXYGEN FLOW FOR A SECOND PREDETERMINED DURATION THAT CORRESPONDS TO │
│            PROVIDING A CERTAIN AMOUNT OF OXYGEN THROUGH THE MASK    │
└─────────────────────────────────────────────────────────────────────┘
                                    ↓
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│              ACTIVATE THE TIMER FOR THE SECOND DURATION             │ ⎯ 509
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ↓
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ IN RESPONSE TO DETERMINING THAT THE TIMER FOR THE SECOND DURATION HAS │ ⎯ 511
│ EXPIRED, SEND, TO THE OXYGEN FLOW CONTROL MECHANISM, AN INDICATION TO │
│                        DISABLE THE OXYGEN FLOW                      │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘

FIG. 5

SYSTEMS AND METHODS OF TRANSFORMING FLUID FLOW OF AN INHALANT ANESTHETIC TO EXPEDITE PATIENT RECOVERY

CROSS REFERENCE TO RELATED APPLICATIONS

This application claims the benefit of U.S. Prov. App. No. 62/887,706, filed Aug. 16, 2019, which is hereby incorporated by reference as if fully set forth herein.

FIELD OF DISCLOSURE

The present disclosure relates generally to the field of analgesia and conscious sedation, and in particular to systems and methods of controlling fluid flow of an inhalant anesthetic to expedite patient recovery.

BACKGROUND

Since the mid-1800's, conscious sedation has been used to relieve pain. Nitrous oxide ($N_2O$) has been the primary inhalant enabling this sedation. Dentistry and oral surgery were some of the first applications of conscious sedation using nitrous oxide and has gained world-wide acceptance for use in emergency rooms, hospitals, ambulances, and doctor offices.

Conscious sedation is a pain-blocking technique that allows a patient to remain partially alert during an invasive procedure. While analgesia is administered, unlike anesthesia, the patient maintains awareness during the procedure. This method of conscious sedation is unique in that patients do not perceive pain and maintain their airways independently. By doing so, the patients have a reduced risk of suppressed respiration associated with the anesthesia.

The use of conscious sedation using nitrous oxide has declined over the years principally due to safety concerns associated with the prolonged exposure to nitrous oxide. Because nitrous oxide is minimally metabolized in humans (with a rate of 0.004%), it retains its potency when exhaled into the room by the patient, and can pose an intoxicating and prolonged exposure hazard to the clinic staff if the room is poorly ventilated. Where nitrous oxide is administered, a continuous-flow fresh-air ventilation system or $N_2O$ scavenger system is used to prevent a waste-gas buildup. The National Institute for Occupational Safety and Health recommends that workers' exposure to nitrous oxide should be controlled during the administration of anesthetic gas in medical, dental and veterinary operators. It set a recommended exposure limit (REL) of 25 ppm (46 $mg/m^3$) to escaped anesthetic. Accordingly, there is a need for improved techniques to reduce the amount of time that a patient is exposed to nitrous oxide during a procedure. In addition, other desirable features and characteristics of the present disclosure will become apparent from the subsequent detailed description and embodiments, taken in conjunction with the accompanying figures and the foregoing technical field and background.

The Background section of this document is provided to place embodiments of the present disclosure in technological and operational context, to assist those of skill in the art in understanding their scope and utility. Unless explicitly identified as such, no statement herein is admitted to be prior art merely by its inclusion in the Background section.

SUMMARY

The following presents a simplified summary of the disclosure in order to provide a basic understanding to those of skill in the art. This summary is not an extensive overview of the disclosure and is not intended to identify key/critical elements of embodiments of the disclosure or to delineate the scope of the disclosure. The sole purpose of this summary is to present some concepts disclosed herein in a simplified form as a prelude to the more detailed description that is presented later.

Briefly described, embodiment of the present disclosure relate to systems and methods of controlling fluid flow of an inhalant anesthetic to expedite patient recovery. According to one aspect, a method is performed by a controller in an inhalant anesthetic system that outputs a nitrous oxide flow and an oxygen flow over different durations for output to a patient mask. The method comprises sending, by the controller, to one of a nitrous oxide flow control mechanism and an oxygen flow control mechanism, an indication to enable a corresponding flow for a first predetermined duration. Further, the method includes sending, by the controller, to the other one of the nitrous oxide flow control mechanism and the oxygen flow control mechanism, an indication to enable the other corresponding flow for a second predetermined duration.

According to another aspect, the method may include activating a timer for the first predetermined duration.

According to another aspect, the method may include sending, by the controller, to the one flow control mechanism, an indication to disable the corresponding flow responsive to determining that the timer for the first predetermined duration has expired.

According to another aspect, the method may include activating a timer for the second predetermined duration.

According to another aspect, sending, by the controller, to the other flow control mechanism, an indication to disable the other corresponding flow responsive to determining that the time for the second predetermined duration has expired.

According to one aspect, a device associated with an inhalant anesthetic system that outputs a nitrous oxide flow and an oxygen flow over different durations for output to a patient mask comprises an oxygen flow control mechanism configured to permit or prevent an oxygen flow. The device also includes a nitrous oxide flow control mechanism configured to permit or prevent a nitrous oxide flow. Further, the device includes a controller operationally coupled to the oxygen flow control mechanism and the nitrous oxide flow control mechanism and is configured to send, to one of the oxygen flow control mechanism and the nitrous oxide flow control mechanism, an indication to enable the corresponding flow for a first predetermined duration. The controller is further configured to activate a timer for the first predetermined duration. In addition, the controller is configured to send, to the one of the oxygen flow control mechanism and the nitrous oxide flow control mechanism, an indication to disable the corresponding flow responsive to determining that the timer for the first predetermined duration has expired.

According to another aspect, the controller may be further configured to send, to the other one of the oxygen flow control mechanism and the nitrous oxide flow control mechanism, an indication to enable the other corresponding flow for a second predetermined duration. The controller may also be configured to activate a timer for the second predetermined duration. In addition, the controller may be configured to send, to the other one of the oxygen flow control mechanism and the nitrous oxide flow control mechanism, an indication to disable the other corresponding flow responsive to determining that the timer for the second predetermined duration has expired.

According to one aspect, a device associated with an inhalant anesthetic system that outputs a nitrous oxide flow and an oxygen flow over different durations for output to a patient mask comprises processing circuitry and memory. Further, the memory contains instructions executable by the processing circuitry. The device is configured to send, to one of an oxygen flow control mechanism and a nitrous oxide flow control mechanism, an indication to enable the corresponding flow for a first predetermined duration. The device is also configured to activate a timer for the first predetermined duration. In addition, the device is configured to send, to the one of the oxygen flow control mechanism and the nitrous oxide flow control mechanism, an indication to disable the corresponding flow responsive to determining that the timer for the first predetermined duration has expired.

According to another aspect, the memory further contains instructions executable by the processing circuitry whereby the device may be further configured to send, to the other one of the oxygen flow control mechanism and the nitrous oxide flow control mechanism, an indication to enable the other corresponding flow for a second predetermined duration. The device may also be configured to activate a timer for the second predetermined duration. In addition, the device may be configured to send, to the other one of the oxygen flow control mechanism and the nitrous oxide flow control mechanism, an indication to disable the other corresponding flow responsive to determining that the timer for the second predetermined duration has expired.

According to one aspect, a computer program comprising instructions which, when executed by at least one processor of a device associated with an inhalant anesthetic system that outputs a nitrous oxide flow and an oxygen flow over different durations for output to a patient mask, causes the device to send, to one of an oxygen flow control mechanism and a nitrous oxide flow control mechanism, an indication to enable the corresponding flow for a first predetermined duration. The device is also configured to activate a timer for the first predetermined duration. In addition, the device is configured to send, to the one of the oxygen flow control mechanism and the nitrous oxide flow control mechanism, an indication to disable the corresponding flow responsive to determining that the timer for the first predetermined duration has expired.

According to another aspect, the device may comprise further instructions which, when executed by the at least one processor of the device, causes the device to send, to the other one of the oxygen flow control mechanism and the nitrous oxide flow control mechanism, an indication to enable the other corresponding flow for a second predetermined duration. Further, the device may include further instructions which may cause the device to activate a timer for the second predetermined duration. In addition, the device may send, to the other one of the oxygen flow control mechanism and the nitrous oxide flow control mechanism, an indication to disable the other corresponding flow responsive to determining that the timer for the second predetermined duration has expired.

According to one aspect, a method performed by a controller in an inhalant anesthetic system that outputs a nitrous oxide flow and an oxygen flow over different durations for output to a patient mask comprises sending, to a nitrous oxide flow control mechanism, an indication to enable a nitrous oxide flow for a first predetermined duration that corresponds to providing a certain amount of nitrous oxide through the mask. Further, the method includes sending, to an oxygen flow control mechanism, an indication to enable an oxygen flow for a second predetermined duration that corresponds to providing a certain amount of oxygen through the mask.

According to another aspect, the method may include activating a timer for the first predetermined duration.

According to another aspect, the method may include sending, to the nitrous oxide flow control mechanism, an indication to disable the nitrous oxide flow responsive to determining that the timer for the first predetermined duration has expired.

According to another aspect, the method may include activating a timer for the second predetermined duration.

According to another aspect, the method may include sending, to the oxygen flow control mechanism, an indication to disable the oxygen flow responsive to determining that the timer for the second predetermined duration has expired.

According to another aspect, the first and second durations are non-overlapping.

According to another aspect, the second predetermined duration occurs after a certain time from an end of the first predetermined duration, with the certain time corresponding to an amount of time required for the nitrous oxide flow to be at least partially absorbed by a patient wearing the patient mask.

According to another aspect, the method may include receiving, from a first flow meter that is operationally coupled between the nitrous oxide flow control mechanism and the mask, an indication of a pressure measurement of the nitrous oxide flow. Further, the method may include determining the first duration based on the pressure measurement of the nitrous oxide flow.

According to another aspect, the method may include receiving, from a second flow meter that is operationally coupled between the oxygen flow control mechanism and the mask, an indication of a pressure measurement of the oxygen flow. Further, the method may include determining the second duration based on the pressure measurement of the oxygen flow.

According to another aspect, the first and second flow meters are the same flow meter.

According to one aspect, a device associated with an inhalant anesthetic system that outputs a nitrous oxide flow and an oxygen flow over different durations for output to a patient mask comprises a nitrous oxide flow control mechanism configured to control the nitrous oxide flow to the mask. The device includes an oxygen flow control mechanism configured to control the oxygen flow to the mask. The device also includes a controller operationally coupled to the nitrous oxide flow control mechanism and the oxygen flow control mechanism. The controller is configured to send, to the nitrous oxide flow control mechanism, an indication to enable the nitrous oxide flow for a first predetermined duration that corresponds to providing a certain amount of nitrous oxide through the mask. The controller is also configured to send, to the oxygen flow control mechanism, an indication to enable the oxygen flow for a second predetermined duration that corresponds to providing a certain amount of oxygen through the mask.

According to another aspect, the controller is further configured to activate a timer for the first predetermined duration.

According to another aspect, the controller is further configured to send, to the nitrous oxide flow control mechanism, an indication to disable the nitrous oxide flow responsive to determining that the timer for the first duration has expired, According to another aspect, the controller is further configured to activate a timer for the second predetermined duration.

According to another aspect, the controller is further configured to send, to the oxygen flow control mechanism, an indication to disable the oxygen flow responsive to determining that the timer for the second duration has expired.

According to another aspect, the device further comprises a first flow meter operationally coupled between the nitrous oxide flow control mechanism and the mask and operable to measure the nitrous oxide flow to the mask. The controller is further configured to receive, from the first flow meter, an indication of a pressure measurement of the nitrous oxide flow. The controller is also configured to determine the first duration based on the pressure measurement of the nitrous oxide flow.

According to another aspect, the device further comprises a second flow meter operationally coupled between the oxygen flow control mechanism and the mask and operable to measure the oxygen flow to the mask. The controller is further configured to receive, from the first flow meter, an indication of a pressure measurement of the nitrous oxide flow. The controller is also configured to determine the first duration based on the pressure measurement of the nitrous oxide flow.

BRIEF DESCRIPTION OF THE DRAWINGS

The present disclosure will now be described more fully hereinafter with reference to the accompanying drawings, in which embodiments of the disclosure are shown. However, this disclosure should not be construed as limited to the embodiments set forth herein. Rather, these embodiments are provided so that this disclosure will be thorough and complete, and will fully convey the scope of the disclosure to those skilled in the art. Like numbers refer to like elements throughout.

FIG. 2 illustrates one embodiment of a method of controlling fluid flow of an inhalant anesthetic to expedite patient recovery in accordance with various aspects as described herein.

FIG. 5 illustrates another embodiment of a method of controlling fluid flow of an inhalant anesthetic to expedite patient recovery in accordance with various aspects as described herein.

DETAILED DESCRIPTION

For simplicity and illustrative purposes, the present disclosure is described by referring mainly to an exemplary embodiment thereof. In the following description, numerous specific details are set forth in order to provide a thorough understanding of the present disclosure. However, it will be readily apparent to one of ordinary skill in the art that the present disclosure may be practiced without limitation to these specific details.

In this disclosure, systems and methods of controlling fluid flow of an inhalant anesthetic to expedite patient recovery are provided. In one embodiment, in an inhalant anesthetic system that includes a nitrous oxide flow and an oxygen flow output through a patient mask, a controller configures a first flow control mechanism to enable the nitrous oxide flow through the mask to the patient during a medical procedure. After completion of the medical procedure, the controller configures the first flow control mechanism to prevent the nitrous oxide flow through the mask to the patient. Further, the controller configures a second flow control mechanism to permit the oxygen flow to the mask for a predetermined duration after completion of the procedure to expedite patent recovery.

In another embodiment, in an inhalant anesthetic system that includes a nitrous oxide flow and an oxygen flow for output through a patient mask, a controller receives, from a first pressure sensor, a pressure measurement of the nitrous oxide flow. The controller then determines that this pressure measurement is lower than an ambient pressure of the nitrous oxide flow so as to indicate that the nitrous oxide flow is being drawn through a patient mask by a patient. In response, the controller controls the first pressure sensor to permit the nitrous oxide flow through the mask. The controller may determine the ambient pressure by receiving, from the first pressure sensor, a pressure measurement of the nitrous oxide flow when the flow control device is configured to prevent the nitrous oxide flow.

In yet another embodiment, in an inhalant anesthetic system that includes a nitrous oxide flow and an oxygen flow for output through a patient mask, a controller receives, from a first pressure sensor, a pressure measurement of the nitrous oxide flow. The controller then determines that this pressure measurement is equivalent to an ambient pressure of the nitrous oxide flow so as to indicate that the nitrous oxide flow is not being drawn through a patient mask by a patient. In response, the controller controls the first pressure sensor to prevent the flow of nitrous oxide to the mask.

In another embodiment, in an inhalant anesthetic system that includes a nitrous oxide flow and an oxygen flow for output through a patient mask, a controller controls a first flow control mechanism to permit a nitrous oxide flow for a first duration and controls a second flow control mechanism to permit an oxygen flow for a second duration.

Figure 1:
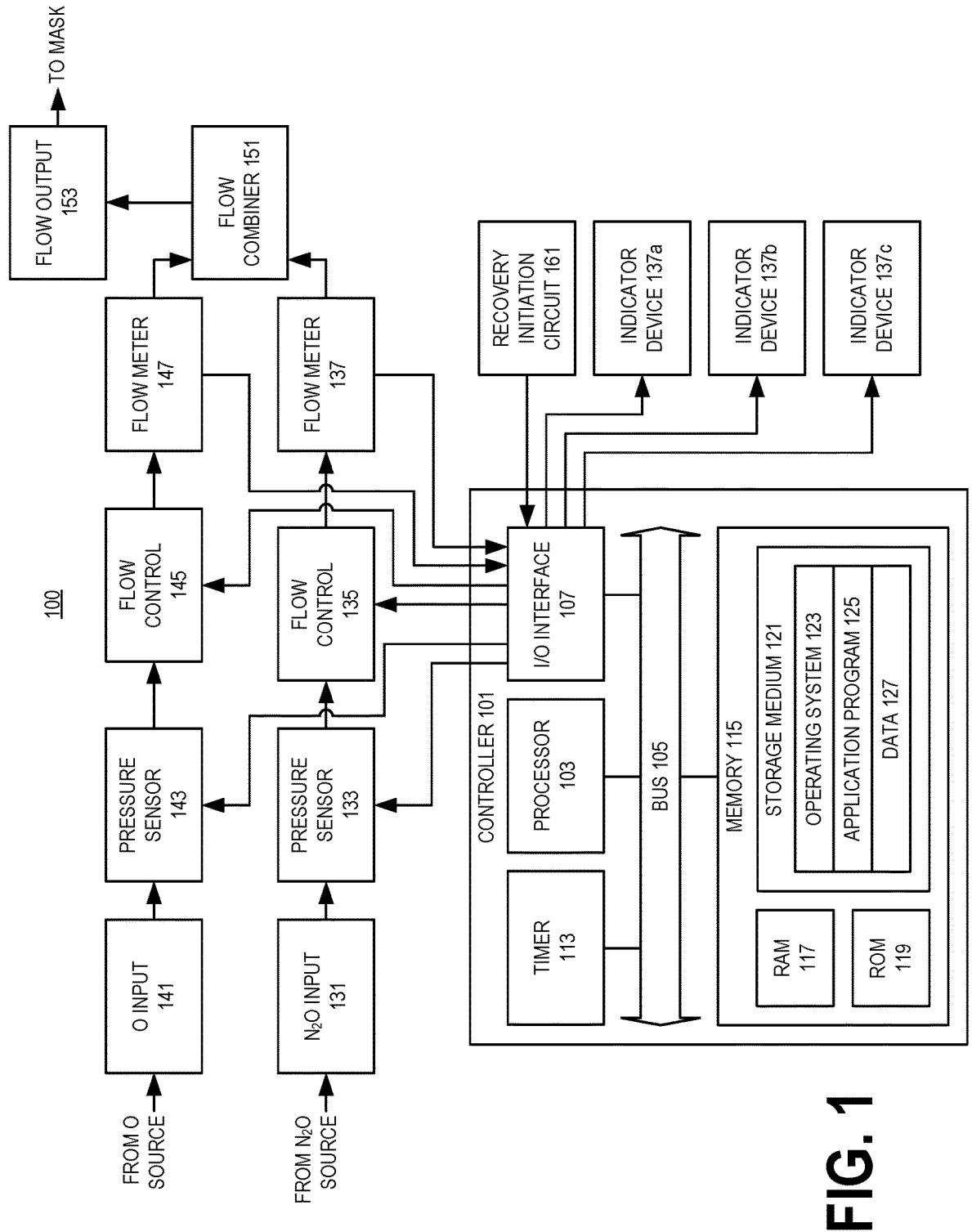
FIG. 1 illustrates one embodiment of a system of controlling fluid flow of an inhalant anesthetic to expedite patient recovery in accordance with various aspects as described herein.

FIG. 1 illustrates one embodiment of a system 100 of controlling fluid flow of an inhalant anesthetic to expedite patient recovery in accordance with various aspects as described herein. In FIG. 1, the system 100 includes a nitrous oxide input device 131, an oxygen input device 141, pressure sensors 133, 143, flow control mechanisms 135, 145, flow meters 137, 147, a flow combiner 151, a flow output device 153, the like, or any combination thereof. The nitrous oxide input device 131 is operable to input nitrous oxide from a nitrous oxide source (e.g., nitrous oxide tank). Further, the nitrous oxide input device 131 is operationally coupled to the nitrous oxide source. In one example, the nitrous oxide input device 131 is a connector that is operable to couple to a connector associated with the nitrous oxide source. The output of the nitrous oxide input device 131 is operationally coupled to the input of the pressure sensor 133. A pressure sensor is operable to measure the flow or pressure of a fluid. The output of the pressure sensor 133 is operationally coupled to the input of the flow control mechanism 135. In one example, a flow control mechanism is operable to enable or disable the flow of a fluid. The output of the flow control mechanism 135 is operationally coupled to the input of the flow meter 137. In one example, a flow meter is operable to measure the flow or pressure of a fluid.

In FIG. 1, the oxygen input device 141 is operable to input oxygen from an oxygen source (e.g., oxygen tank). The input of the oxygen input device 141 is operationally coupled to the oxygen source. In one example, the oxygen input device 141 is a connector that is operable to be coupled to a connector associated with the oxygen source. The output of the oxygen input device 141 is operationally coupled to the input of the pressure sensor 143. The output of the pressure sensor 143 is operationally coupled to the input of the flow control mechanism 145. The output of the flow control mechanism is operationally coupled to the input of the flow meter 147. The output of each flow meter 137, 147 is operationally coupled to respective inputs of the flow combiner 151. In one example, a flow combiner combines first and second flows to obtain a combined flow. The output of the flow combiner 151 is operationally coupled to the input of the flow output device 153. The flow output device 153 is configured to output the combined flow through a patient mask. In one example, the flow output device 153 is a connector that is operable to couple to a connector associated with the patient mask.

In the current embodiment, the system 100 also includes a controller 101, indicator devices 137a-c, a recovery initiation circuit 161, the like, or any combination thereof. The indicator devices 137a-c are operable to provide a visual indication. In one example, the indicator device 137a-c is a light source (e.g., LED). In another example, the indicator device 137a-c is a display that displays the visual indication. In yet another example, an indicator device is a sound source (e.g., speaker) that provides an audible indication. The recovery initiation circuit 161 is operable to indicate to the controller 101 that the system 100 is to provide only the oxygen flow to the mask. In one example, the recovery initiation circuit 161 is a switch mechanism (e.g., push button) that, once activated or enabled, causes a temporary change in the state of the recovery initiation circuit 161. Further, the controller 101 is operable to detect the recovery initiation circuit 161 being activated or enabled and in response, is operable to determine to provide only the oxygen flow to the mask.

In FIG. 1, the controller 101 includes processing circuitry 103 that is operatively coupled to input/output interface 107, a timer 113, memory 115 including random access memory (RAM) 117, read-only memory (ROM) 119, and storage medium 121 or the like, a power source (not shown), and/or any other component, or any combination thereof. The storage medium 121 includes operating system 123, application program 125, and data 127. In other embodiments, storage medium 121 may include other similar types of information. The controller 101 may utilize all of the components shown in FIG. 1, or only a subset of the components. The level of integration between the components may vary from one controller to another controller. Further, certain controllers may contain multiple instances of a component, such as multiple processors, memories, transceivers, transmitters, receivers, etc.

In FIG. 1, the processing circuitry 101 may be configured to process computer instructions and data. The processing circuitry 101 may be configured to implement any sequential state machine operative to execute machine instructions stored as machine-readable computer programs in the memory, such as one or more hardware-implemented state machines (e.g., in discrete logic, field-programmable gate array (FPGA), application-specific integrated circuit (ASIC), etc.); programmable logic together with appropriate firmware; one or more stored program, general-purpose processors, such as a microprocessor or digital signal processor (DSP), together with appropriate software; or any combination of the above. For example, the processing circuitry 101 may include two central processing units (CPUs). Data may be information in a form suitable for use by a computer.

In the depicted embodiment, input/output interface 107 may be configured to provide a communication interface to an input device, output device, or input and output device. The controller 101 may be configured to use an output device via input/output interface 107. An output device may use the same type of interface port as an input device. The input/output interface 107 may include one or more general purpose input/output components that are each operable to control or monitor other circuitry. In one example, a general purpose input/output component may be configured to enable or disable the operation of or power to other circuitry. In another example, a general purpose input/output component may be configured to read the state of a switch. In yet another example, a general purpose input/output component may be configured to drive a light emitting diode (LED). A skilled artisan will recognize the many different uses a general purpose input/output components.

In FIG. 1, the RAM 117 may be configured to interface via bus 105 to processing circuitry 101 to provide storage or caching of data or computer instructions during the execution of software programs such as the operating system, application programs, and device drivers. ROM 119 may be configured to provide computer instructions or data to processing circuitry 101. For example, the ROM 119 may be configured to store invariant low-level system code or data for basic system functions such as basic input and output (I/O), startup, or reception of keystrokes from a keyboard that are stored in a non-volatile memory. The storage medium 121 may be configured to include memory such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, or flash drives. In one example, the storage medium 121 may be configured to include operating system 123, application program 125 such as a web browser application, a widget or gadget engine or another application, and data file 127. The storage medium 121 may store, for use by the controller 101, any of a variety of various operating systems or combinations of operating systems.

The storage medium 121 may be configured to include a number of physical drive units, such as redundant array of independent disks (RAID), floppy disk drive, flash memory, USB flash drive, external hard disk drive, thumb drive, pen drive, key drive, high-density digital versatile disc (HD-DVD) optical disc drive, internal hard disk drive, Blu-Ray optical disc drive, holographic digital data storage (HDDS) optical disc drive, external mini-dual in-line memory module (DIMM), synchronous dynamic random access memory (SDRAM), external micro-DIMM SDRAM, smartcard memory such as a subscriber identity module or a removable user identity (SIM/RUIM) module, other memory, or any combination thereof. The storage medium 121 may allow the controller 101 to access computer-executable instructions, application programs or the like, stored on transitory or non-transitory memory media, to off-load data, or to upload data. An article of manufacture, such as one utilizing a communication system may be tangibly embodied in storage medium 121, which may comprise a device readable medium. The power source may be configured to provide alternating current (AC) or direct current (DC) power to components of system 100.

The features, benefits and/or functions described herein may be implemented in one of the components of the system 100 or partitioned across multiple components of the system 100. Further, the features, benefits, and/or functions described herein may be implemented in any combination of hardware, software or firmware.

Those skilled in the art will also appreciate that embodiments herein further include corresponding computer programs.

A computer program comprises instructions which, when executed on at least one processor of an apparatus, cause the apparatus to carry out any of the respective processing described above. A computer program in this regard may comprise one or more code modules corresponding to the means or units described above. The computer program may be embodied on a non-transitory storage medium.

Embodiments further include a carrier containing such a computer program. This carrier may comprise one of an electronic signal, optical signal, radio signal, or computer readable storage medium.

In this regard, embodiments herein also include a computer program product stored on a non-transitory computer readable (storage or recording) medium and comprising instructions that, when executed by a processor of an apparatus, cause the apparatus to perform as described above.

Embodiments further include a computer program product comprising program code portions for performing the steps of any of the embodiments herein when the computer program product is executed by a computing device. This computer program product may be stored on a computer readable recording medium.

Additional embodiments will now be described. At least some of these embodiments may be described as applicable in certain contexts for illustrative purposes, but the embodiments are similarly applicable in other contexts not explicitly described.

FIG. 2 illustrates one embodiment of a method 200 of controlling fluid flow of an inhalant anesthetic to expedite patient recovery in accordance with various aspects as described herein. In FIG. 2, the method 200 may start, for instance, at block 201, where it includes receiving an indication to provide only the oxygen flow to the mask so as to expedite patient recovery from inhalation of the nitrous oxide. The indication may be received, for example, from a patient recovery initiation circuit that is operationally coupled to the controller. In one example, the patient recovery initiation circuit is a switch mechanism (e.g., push button) that, once activated or enabled, causes a temporary change in the state of the recovery initiation circuit. In block 203, the method includes determining to provide only the oxygen flow to the mask based on the received indication. In block 205, the method 200 includes activating a timer for a predetermined duration associated with providing only the oxygen flow to the mask.

In block 207, the method 200 may include sending, to a nitrous oxide flow control mechanism, an indication to prevent the flow of nitrous oxide to the mask. In one example, the nitrous oxide flow control mechanism is operable to permit or prevent the nitrous oxide flow to the mask. In block 209, the method 200 may include receiving, from a nitrous oxide flow meter, an indication of a pressure measurement associated with the nitrous oxide flow. In one example, the flow meter is disposed after the flow control mechanism. In block 211, the method 200 may including determining that the nitrous oxide flow control mechanism is configured to prevent the nitrous oxide flow to the mask based on the pressure measurement. In block 213, the method 200 may include sending an indication that only the oxygen flow is output to the mask. The indication may be sent, for example, to an indicator device (e.g., LED) operationally coupled to the controller. In block 215, the method 200 may include sending, to an oxygen flow control mechanism, an indication to prevent the flow of oxygen in response to determining that the timer has expired.

Figure 3:
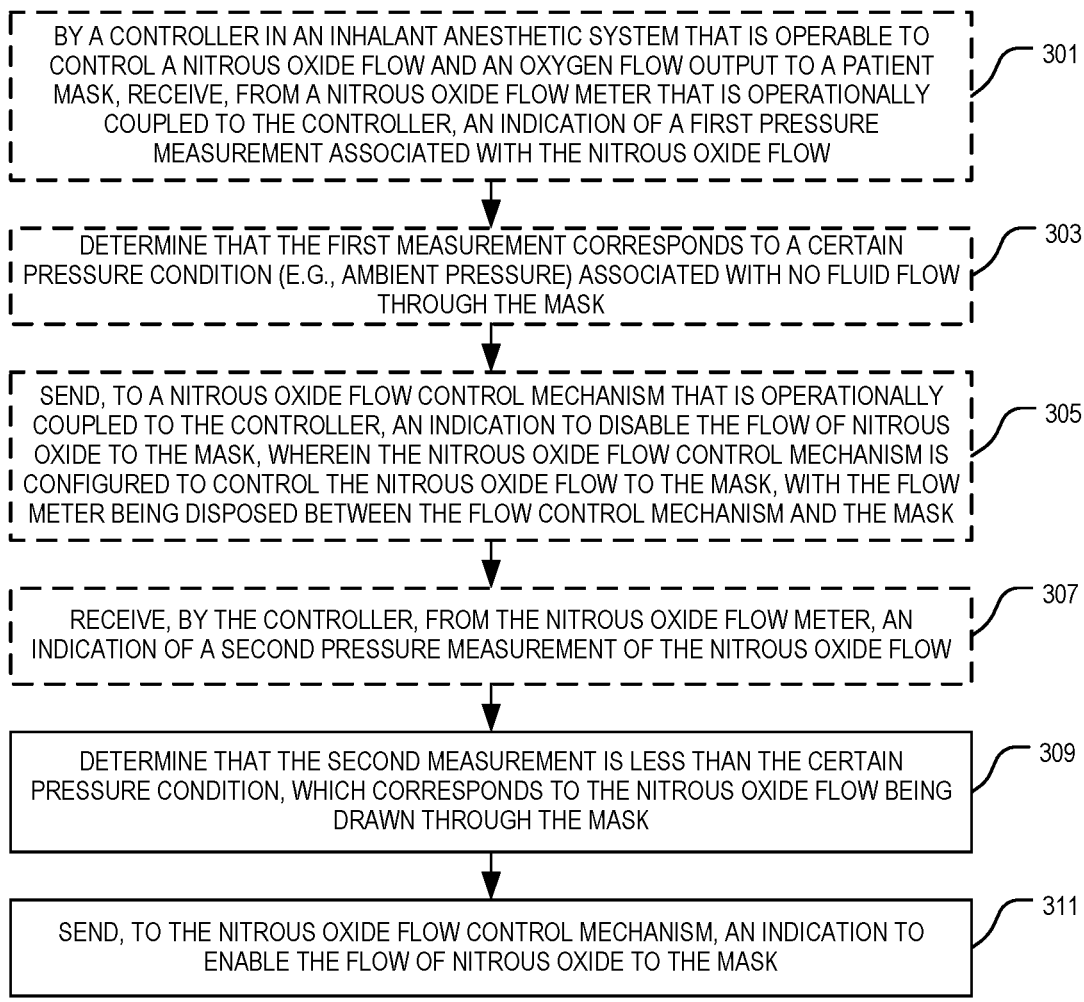
FIG. 3 illustrates another embodiment of a method of controlling fluid flow of an inhalant anesthetic to expedite patient recovery in accordance with various aspects as described herein.

FIG. 3 illustrates another embodiment of a method 300 of controlling fluid flow of an inhalant anesthetic to expedite patient recovery in accordance with various aspects as described herein. In FIG. 3, the method may start, for instance, at block 301 where it may include receiving, from a nitrous oxide flow meter, an indication of a first pressure measurement associated with the nitrous oxide flow. In block 303, the method 300 may include determining that the first measurement is equivalent to a predetermined pressure (e.g., ambient pressure) associated with the nitrous oxide flow not being drawn via the mask. In block 305, the method 300 may include sending, to a nitrous oxide flow control mechanism, an indication to prevent the flow of nitrous oxide to the mask. The nitrous oxide flow control mechanism is configured to permit or prevent the nitrous oxide flow to the mask. Further, the nitrous oxide flow meter may be disposed after the nitrous oxide flow control mechanism.

In block 307, the method may include receiving, from the nitrous oxide flow meter, an indication of a second pressure measurement of the nitrous oxide flow. In block 309, the method 300 includes determining that the second pressure measurement is less than the predetermined pressure so as to indicate that the nitrous oxide flow is being drawn through the mask. In block 311, the method 300 including sending, to the nitrous oxide flow control mechanism, an indication to permit the flow of nitrous oxide through the mask.

Figure 4:
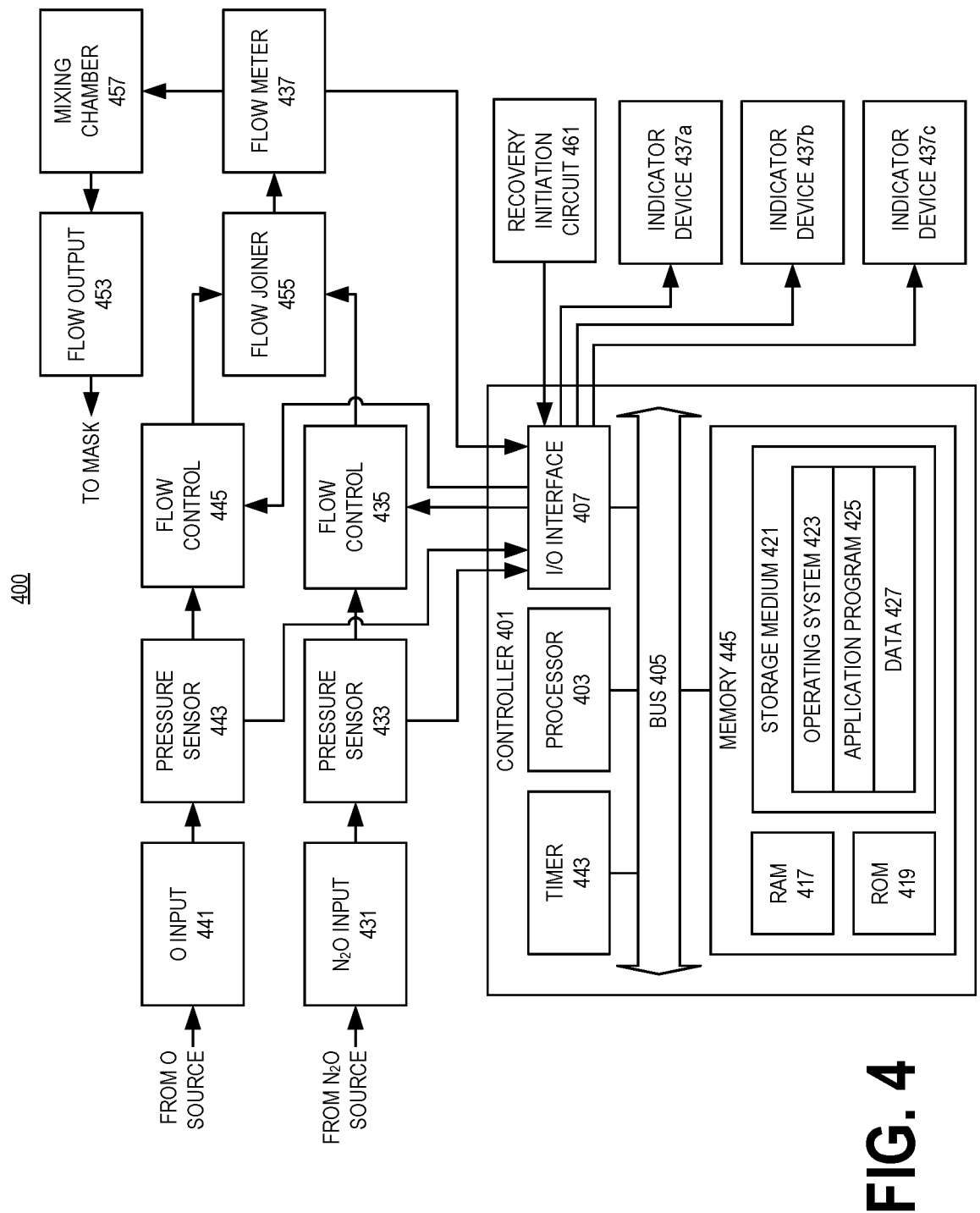
FIG. 4 illustrates another embodiment of a system of controlling fluid flow of an inhalant anesthetic to expedite patient recovery in accordance with various aspects as described herein.

FIG. 4 illustrates one embodiment of a system 400 of controlling fluid flow of an inhalant anesthetic to expedite patient recovery in accordance with various aspects as described herein. In FIG. 4, the system 400 includes a nitrous oxide input device 431, an oxygen input device 441, pressure sensors 433, 443, flow control mechanisms 435, 445, flow joiner 455, flow meter 437, a mixing chamber 457, a flow output device 453, the like, or any combination thereof. The nitrous oxide input device 431 is operable to input nitrous oxide from a nitrous oxide source (e.g., nitrous oxide tank). Further, the nitrous oxide input device 431 is operable to be operationally coupled to the nitrous oxide source. In one example, the nitrous oxide input device 431 is a connector that is operable to couple to a connector associated with the nitrous oxide source. The output of the nitrous oxide input device 431 is operationally coupled to the input of the pressure sensor 433. In one example, a pressure sensor is operable to increase or decrease the flow or pressure of a fluid to a certain flow or pressure. In one example, a pressure sensor is a flow regulator. The output of the pressure sensor 433 is operationally coupled to the input of the flow control mechanism 435. A flow control mechanism is, for example, a non-return value. In one example, a flow control mechanism is operable to enable or disable the flow of a fluid.

In FIG. 4, the oxygen input device 441 is operable to input oxygen from an oxygen source (e.g., oxygen tank). The input of the oxygen input device 441 is operationally coupled to the oxygen source. In one example, the oxygen input device 441 is a connector that is operable to be coupled to a connector associated with the oxygen source. The output of the oxygen input device 441 is operationally coupled to the input of the pressure sensor 443. The output of the pressure sensor 443 is operationally coupled to the input of the flow control mechanism 445.

The output of each flow control mechanism 435, 445 is operationally coupled to respective inputs of the flow joiner 455. In one example, a flow joiner joins first and second flows to obtain a single output flow. The output of the flow joiner 455 is operationally coupled to the input of the flow meter 437. In one example, a flow meter is operable to measure the flow or pressure of a fluid. The output of flow meter 437 is operationally coupled to the input of the mixing chamber 457. In one example, a mixing chamber mixes first and second flows to obtain a mixed flow. The output of the mixing chamber 457 is operationally coupled to the input of the flow output device 453. The flow output device 453 is configured to output the mixed flow to a patient mask. Accordingly, the output of the flow output device 453 is operable to be coupled to the patient mask. In one example, the flow output device 453 is a connector that is operable to couple to a connector associated with the patient mask.

In the current embodiment, the system 400 also includes a controller 401, indicator devices 437a-c, a recovery initiation circuit 461, the like, or any combination thereof. The indicator devices 437a-c are operable to provide an indication. In one example, an indicator device is a light source (e.g., LED). In another example, an indicator device is a display that displays an indication. In yet another example, an indicator device is a sound source (e.g., speaker) that provides an audible indication. The recovery initiation circuit 461 is operable to indicate to the controller 401 that the system 400 is to provide only the oxygen flow to the mask. In one example, the recovery initiation circuit 461 is a switch mechanism (e.g., push button) that, once activated or enabled, causes a temporary change in the state of the recovery initiation circuit 461. Further, the controller 401 is operable to detect the recovery initiation circuit 461 being activated or enabled and in response, is operable to determine to provide only the oxygen flow to the mask.

In FIG. 4, the controller 401 includes processing circuitry 403 that is operatively coupled to input/output interface 407, a timer 443, memory 445 including random access memory (RAM) 417, read-only memory (ROM) 419, and storage medium 421 or the like, a power source (not shown), and/or any other component, or any combination thereof. The storage medium 421 includes operating system 423, application program 425, and data 427. In other embodiments, storage medium 421 may include other similar types of information. The controller 401 may utilize all of the components shown in FIG. 4, or only a subset of the components. The level of integration between the components may vary from one controller to another controller. Further, certain controllers may contain multiple instances of a component, such as multiple processors, memories, transceivers, transmitters, receivers, etc.

In FIG. 4, the processing circuitry 401 may be configured to process computer instructions and data. The processing circuitry 401 may be configured to implement any sequential state machine operative to execute machine instructions stored as machine-readable computer programs in the memory, such as one or more hardware-implemented state machines (e.g., in discrete logic, FPGA, ASIC, etc.); programmable logic together with appropriate firmware; one or more stored program, general-purpose processors, such as a microprocessor or digital signal processor (DSP), together with appropriate software; or any combination of the above. For example, the processing circuitry 401 may include two central processing units (CPUs). Data may be information in a form suitable for use by a computer.

In the depicted embodiment, input/output interface 407 may be configured to provide a communication interface to an input device, output device, or input and output device. The controller 401 may be configured to use an output device via input/output interface 407. An output device may use the same type of interface port as an input device. The input/output interface 407 may include one or more general purpose input/output components that are each operable to control or monitor other circuitry. In one example, a general purpose input/output component may be configured to enable or disable the operation of or power to other circuitry. In another example, a general purpose input/output component may be configured to read the state of a switch. In yet another example, a general purpose input/output component may be configured to drive a light emitting diode (LED). A skilled artisan will recognize the many different uses a general purpose input/output components.

In FIG. 4, the RAM 417 may be configured to interface via bus 405 to processing circuitry 401 to provide storage or caching of data or computer instructions during the execution of software programs such as the operating system, application programs, and device drivers. ROM 419 may be configured to provide computer instructions or data to processing circuitry 401. For example, the ROM 419 may be configured to store invariant low-level system code or data for basic system functions such as basic input and output (I/O), startup, or reception of keystrokes from a keyboard that are stored in a non-volatile memory. The storage medium 421 may be configured to include memory such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, or flash drives. In one example, the storage medium 421 may be configured to include operating system 423, application program 425 such as a web browser application, a widget or gadget engine or another application, and data file 427. The storage medium 421 may store, for use by the controller 401, any of a variety of various operating systems or combinations of operating systems.

The storage medium 421 may be configured to include a number of physical drive units, such as redundant array of independent disks (RAID), floppy disk drive, flash memory, USB flash drive, external hard disk drive, thumb drive, pen drive, key drive, high-density digital versatile disc (HD-DVD) optical disc drive, internal hard disk drive, Blu-Ray optical disc drive, holographic digital data storage (HDDS) optical disc drive, external mini-dual in-line memory module (DIMM), synchronous dynamic random access memory (SDRAM), external micro-DIMM SDRAM, smartcard memory such as a subscriber identity module or a removable user identity (SIM/RUIM) module, other memory, or any combination thereof. The storage medium 421 may allow the controller 401 to access computer-executable instructions, application programs or the like, stored on transitory or non-transitory memory media, to off-load data, or to upload data. An article of manufacture, such as one utilizing a communication system may be tangibly embodied in storage medium 421, which may comprise a device readable medium. The power source may be configured to provide alternating current (AC) or direct current (DC) power to components of system 400.

The features, benefits and/or functions described herein may be implemented in one of the components of the system 400 or partitioned across multiple components of the system 400. Further, the features, benefits, and/or functions described herein may be implemented in any combination of hardware, software or firmware.

FIG. 5 illustrates another embodiment of a method of controlling fluid flow of an inhalant anesthetic to expedite patient recovery in accordance with various aspects as described herein. In FIG. 5, the method 500 may start, for instance, at block 501 where it includes sending, to a nitrous oxide flow control mechanism, an indication to permit the nitrous oxide flow for a first predetermined duration. In block 503, the method 500 may include activating a timer for the first duration. In block 505, the method 500 may include sending, to the nitrous oxide flow control mechanism, an indication to prevent the nitrous oxide flow in response to determining that the timer for the first duration has expired.

In block 507, the method 500 includes sending, to the oxygen flow control mechanism, an indication to enable the oxygen flow for a second predetermined duration. In block 509, the method 500 may include activating a timer for the second duration. In block 511, the method 500 may include sending, to the oxygen flow control mechanism, an indication to disable the oxygen flow in response to determining that the timer for the second duration has expired.

Figure 6:
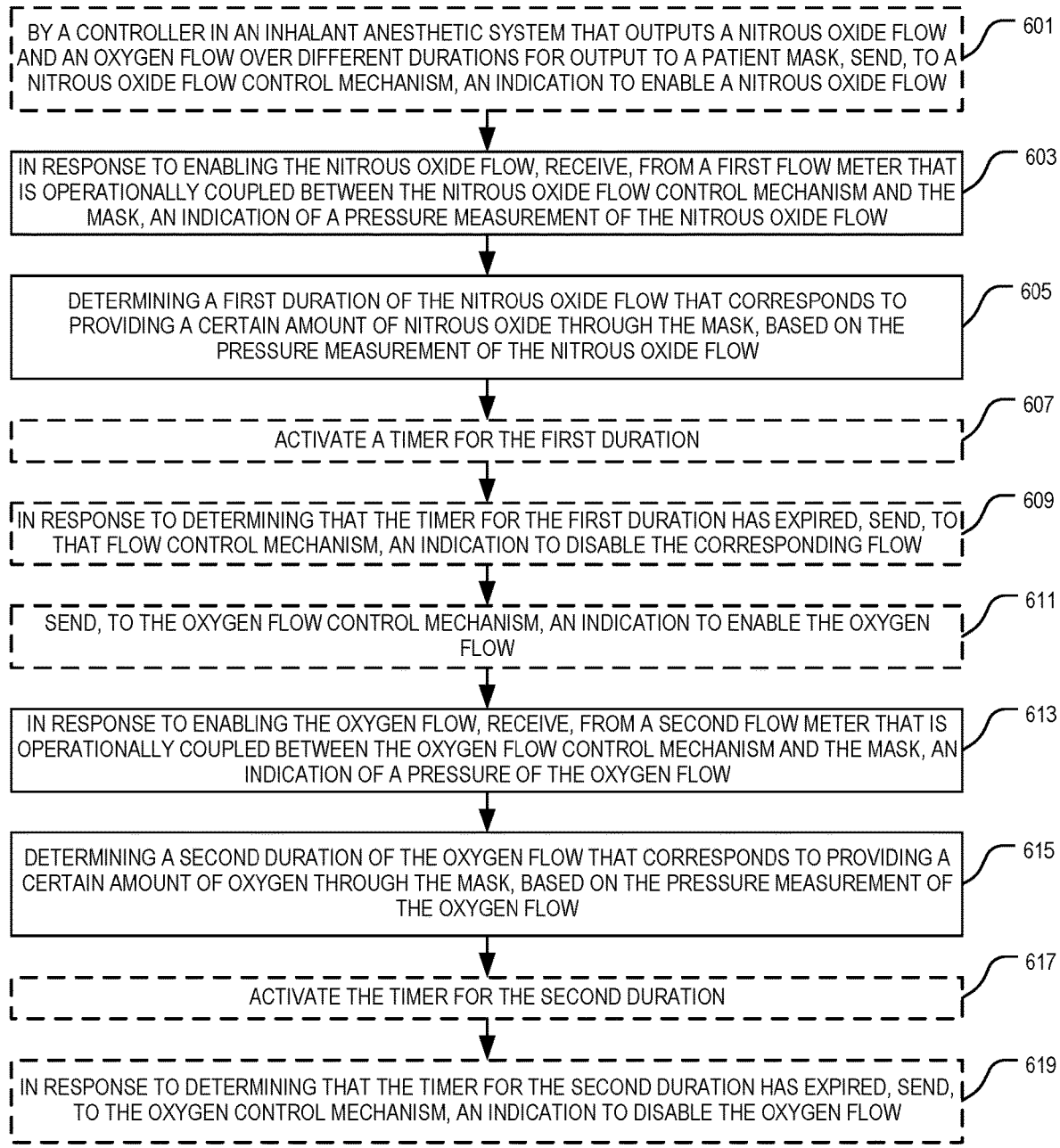
FIG. 6 illustrates another embodiment of a method of controlling fluid flow of an inhalant anesthetic to expedite patient recovery in accordance with various aspects as described herein.

FIG. 6 illustrates another embodiment of a method 600 of controlling fluid flow of an inhalant anesthetic to expedite patient recovery in accordance with various aspects as described herein. In FIG. 6, the method 600 may start, for instance, at block 601 where it may include sending, to a nitrous oxide flow control mechanism, an indication to enable a nitrous oxide flow. At block 603, the method 600 includes receiving, from a first flow meter that is operationally coupled to the nitrous oxide flow control mechanism, an indication of a pressure measurement of the nitrous oxide flow responsive to enabling the nitrous oxide flow. At block 605, the method 600 includes determining a first duration of the nitrous oxide flow based on the pressure measurement of that flow. A skilled artisan will readily recognize various techniques for calculating an amount of fluid delivered at a certain pressure for a certain duration.

In FIG. 6, at block 607, the method 600 may include activating a timer for the first duration. In response to determining that the timer for the first duration has expired, the method 600 may include sending, to the flow control mechanism, an indication to disable the corresponding flow, as represented by block 609. At block 611, the method 600 may send, to the oxygen flow control mechanism, an indication to enable the oxygen flow. In response to enabling the oxygen flow, the method 600 receives, from a second flow meter that is operationally coupled between the oxygen flow control mechanism and the mask, an indication of a pressure of the oxygen flow, as represented by block 613. The first and second flow meters may be the same flow meter or different flow meters. At block 615, the method 600 includes determining a second duration of the oxygen flow that corresponds to providing a certain amount of oxygen through the mask, based on the pressure measurement of the oxygen flow. At block 617, the method 600 may include activating the timer for the second duration. In response to determining that the timer for the second duration has expired, the method 600 may include sending to the oxygen control mechanism, an indication to disable the oxygen flow, as represented by block 619.

The previous detailed description is merely illustrative in nature and is not intended to limit the present disclosure, or the application and uses of the present disclosure. Furthermore, there is no intention to be bound by any expressed or implied theory presented in the preceding field of use, background, summary, or detailed description. The present disclosure provides various examples, embodiments and the like, which may be described herein in terms of functional or logical block elements. The various aspects described herein are presented as methods, devices (or apparatus), systems, or articles of manufacture that may include a number of components, elements, members, modules, nodes, peripherals, or the like. Further, these methods, devices, systems, or articles of manufacture may include or not include additional components, elements, members, modules, nodes, peripherals, or the like.

Furthermore, the various aspects described herein may be implemented using standard programming or engineering techniques to produce software, firmware, hardware (e.g., circuits), or any combination thereof to control a computing device to implement the disclosed subject matter. It will be appreciated that some embodiments may be comprised of one or more generic or specialized processors such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the methods, devices and systems described herein. Alternatively, some or all functions could be implemented by a state machine that has no stored program instructions, or in one or more application specific integrated circuits (ASICs), in which each function or some combinations of certain of the functions are implemented as custom logic circuits. Of course, a combination of the two approaches may be used. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The term "article of manufacture" as used herein is intended to encompass a computer program accessible from any computing device, carrier, or media. For example, a computer-readable medium may include: a magnetic storage device such as a hard disk, a floppy disk or a magnetic strip; an optical disk such as a compact disk (CD) or digital versatile disk (DVD); a smart card; and a flash memory device such as a card, stick or key drive. Additionally, it should be appreciated that a carrier wave may be employed to carry computer-readable electronic data including those used in transmitting and receiving electronic data such as electronic mail (e-mail) or in accessing a computer network such as the Internet or a local area network (LAN). Of course, a person of ordinary skill in the art will recognize many modifications may be made to this configuration without departing from the scope or spirit of the subject matter of this disclosure.

Throughout the specification and the embodiments, the following terms take at least the meanings explicitly associated herein, unless the context clearly dictates otherwise. Relational terms such as "first" and "second," and the like may be used solely to distinguish one entity or action from another entity or action without necessarily requiring or implying any actual such relationship or order between such entities or actions. The term "or" is intended to mean an inclusive "or" unless specified otherwise or clear from the context to be directed to an exclusive form. Further, the terms "a," "an," and "the" are intended to mean one or more unless specified otherwise or clear from the context to be directed to a singular form. The term "include" and its various forms are intended to mean including but not limited to. References to "one embodiment," "an embodiment," "example embodiment," "various embodiments," and other like terms indicate that the embodiments of the disclosed technology so described may include a particular function, feature, structure, or characteristic, but not every embodiment necessarily includes the particular function, feature, structure, or characteristic. Further, repeated use of the phrase "in one embodiment" does not necessarily refer to the same embodiment, although it may. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. A device or structure that is "configured" in a certain way is configured in at least that way, but may also be configured in ways that are not listed.

What is claimed is:

1. A method performed by a controller in an inhalant anesthetic system that outputs a nitrous oxide flow and an oxygen flow over different durations for output to a patient mask, comprising:
sending, to a nitrous oxide flow control mechanism, an indication to enable only a nitrous oxide flow for a first predetermined duration that corresponds to providing a certain amount of nitrous oxide through the mask; and
sending, to an oxygen flow control mechanism, an indication to enable an oxygen flow for a second predetermined duration that corresponds to providing a certain amount of oxygen through the mask,
wherein the oxygen flow is disabled during the first predetermined duration.

2. The method of claim 1, further comprising:
activating a timer for the first predetermined duration.

3. The method of claim 2, further comprising:
in response to determining that the timer for the first predetermined duration has expired, sending, to the nitrous oxide flow control mechanism, an indication to disable the nitrous oxide flow.

4. The method of claim 1, further comprising:
activating a timer for the second predetermined duration.

5. The method of claim 4, further comprising:
in response to determining that the timer for the second predetermined duration has expired, sending, to the oxygen flow control mechanism, an indication to disable the oxygen flow.

6. The method of claim 1, wherein the first and second durations correspond to non-overlapping time periods.

7. The method of claim 1, wherein the second predetermined duration corresponds to a time period that occurs after a certain time from an end of a time period that corresponds to the first predetermined duration, the certain time corresponding to an amount of time required for the nitrous oxide flow to be at least partially absorbed by a patient wearing the patient mask.

8. The method of claim 1, further comprising:
receiving, from a first flow meter that is operationally coupled between the nitrous oxide flow control mechanism and the mask, an indication of a pressure measurement of the nitrous oxide flow; and
determining the first duration based on the pressure measurement of the nitrous oxide flow.

9. The method of claim 8, further comprising:
receiving, from a second flow meter that is operationally coupled between the oxygen flow control mechanism and the mask, an indication of a pressure measurement of the oxygen flow; and
determining the second duration based on the pressure measurement of the oxygen flow.

10. The method of claim 9, wherein the first and second flow meters are the same flow meter and the first and second durations correspond to non-overlapping time periods.

11. A device associated with an inhalant anesthetic system that outputs a nitrous oxide flow and an oxygen flow over different durations for output to a patient mask, comprising:
a nitrous oxide flow control mechanism configured to control the nitrous oxide flow to the mask;
an oxygen flow control mechanism configured to control the oxygen flow to the mask; and
a controller operationally coupled to the nitrous oxide flow control mechanism and the oxygen flow control mechanism, and configured to:
send, to the nitrous oxide flow control mechanism, an indication to enable only the nitrous oxide flow for a first predetermined duration that corresponds to providing a certain amount of nitrous oxide through the mask; and
send, to the oxygen flow control mechanism, an indication to enable the oxygen flow for a second predetermined duration that corresponds to providing a certain amount of oxygen through the mask,
wherein the oxygen flow is disabled during the first predetermined duration.

12. The device of claim 11, wherein the controller is further configured to:
activate a timer for the first predetermined duration.

13. The device of claim 12, wherein the controller is further configured to:
in response to determining that the timer for the first duration has expired, send, to the nitrous oxide flow control mechanism, an indication to disable the nitrous oxide flow.

14. The device of claim 11, wherein the controller is further configured to:
activate a timer for the second predetermined duration.

15. The device of claim 14, wherein the controller is further configured to:
in response to determining that the timer for the second duration has expired, send, to the oxygen flow control mechanism, an indication to disable the oxygen flow.

16. The device of claim 11, wherein the first and second durations correspond to non-overlapping time periods.

17. The device of claim 11, wherein the second predetermined duration corresponds to a time period that occurs after a certain time from an end of a time period that corresponds to the first predetermined duration, the certain time corresponding to an amount of time required for the nitrous oxide flow to be at least partially absorbed by a patient wearing the patient mask.

18. The device of claim 11, further comprising:
a first flow meter operationally coupled between the nitrous oxide flow control mechanism and the mask and operable to measure the nitrous oxide flow to the mask; and
wherein the controller is further configured to:
receive, from the first flow meter, an indication of a pressure measurement of the nitrous oxide flow; and
determine the first duration based on the pressure measurement of the nitrous oxide flow.

19. The device of claim 18, further comprising:
a second flow meter operationally coupled between the oxygen flow control mechanism and the mask and operable to measure the oxygen flow to the mask; and
wherein the controller is further configured to:
receive, from the second flow meter, an indication of a pressure measurement of the oxygen flow; and
determine the second duration based on the pressure measurement of the oxygen flow.

20. The device of claim 19, wherein the first and second flow meters are the same flow meter and the first and second durations correspond to non-overlapping time periods.

\* \* \* \* \*